US00PP25010P3

(12) United States Plant Patent
Zaiger et al.

(10) Patent No.: US PP25,010 P3
(45) Date of Patent: Oct. 28, 2014

(54) NECTARINE TREE NAME 'AMBER FIRE'

(50) Latin Name: ***Prunus persica* var. *nucipersica***
Varietal Denomination: Amber Fire

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 181 days.

(21) Appl. No.: 13/694,407

(22) Filed: Nov. 30, 2012

(65) Prior Publication Data

US 2014/0157463 P1 Jun. 5, 2014

(51) Int. Cl.
*A01H 5/00* (2006.01)

(52) U.S. Cl.
USPC ..... Plt./190

(58) Field of Classification Search
CPC . A01H 5/0856; A01H 5/0837; A01H 5/0831; A01H 5/08
USPC ..... Plt./190
See application file for complete search history.

*Primary Examiner* — June Hwu

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Tree having a low winter chilling requirement of approximately 150 hours at or below 45° F.
3. Fruit ripening in the early maturity season.
4. Fruit with a high degree of attractive dark red skin color.
5. Heavy and regular production of medium to large size fruit.
6. Firm, yellow flesh with good flavor and eating quality.

1 Drawing Sheet

Botanical designation: *Prunus persica* var. *nucipersica*.
Variety denomination: 'AMBER FIRE'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine and proprietary seedling selections, which are known to us, and mentioned herein, 'Honey May' Nectarine (U.S. Plant Pat. No. 19,363) and the proprietary non-patented nectarine seedling selections '58ZA720', '56ZC700', '374LH278', '2LG119' and '57ZA1067'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modesto, Calif. as a first generation cross between two non-patented proprietary nectarine seedling selections with the field identification numbers '58ZA720' and '56ZC700'. The seed parent (58ZA720) nectarine (non-patented) originated as a first generation cross between '2LG119' nectarine (non-patented) and '374LH278' nectarine (non-patented). The pollen parent (56ZC700) nectarine (non-patented) originated as an open pollinated seedling selection from our proprietary non-patented nectarine seedling selection '57ZA1067'. A large group of these first generation crosses were grown on their own root system and under close and careful observation we recognized the desirable fruit and tree characteristics of the present new variety and selected it in 2007 for further asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree is of large size, vigorous, upright growth and a regular and productive bearer of medium to large size, firm, yellow flesh, clingstone fruit with good handling and shipping quality. The fruit is further characterized by having moderately juicy flesh, an attractive dark red skin color and good eating quality. In comparison to its seed parent (58ZA720) nectarine (non-patented) the fruit of the new variety has a more attractive dark red skin color and is approximately 13 days earlier in maturity. In comparison to its pollen parent (56ZC700) nectarine (non-patented) the fruit of the new variety is larger in size. In comparison to the commercial nectarine variety 'Honey May' (U.S. Plant Pat. No. 19,363) the fruit of the new variety has a more attractive dark red skin color, the tree blooms approximately 4 days earlier with a lower winter chilling requirement of approximately 50 hours at or below 45° F.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 5 year old specimens grown near Modesto, Calif., with color in accordance with Munsell Book of Color published in 1958.

Tree:

*Size.*—Large, usually pruned to 3 to 3.5 meters in height and width for economical harvesting of fruit. Size varies with different cultural practices.

*Vigor.*—Vigorous, growth of 1.5 to 2.5 meters the first growing season. Varies slightly with type of soil, fertility and climatic conditions.

*Form.*—Upright, usually pruned to vase shape.

*Branching habit.*—Upright, crotch angle approximately 35°, increases with heavy crop load.

*Productivity.*—Productive, normal fruit thinning necessary for market size fruit. Fruit set varies with climatic conditions during bloom season.

*Bearer.*—Regular, adequate fruit set 4 consecutive years. No alternate bearing observed.

*Fertility.*—Self-fertile.

*Density.*—Medium dense, pruning to open center of tree to vase shape desirable to enhance fruit color and keep fruit wood healthy.

*Hardiness.*—Hardy in all stone fruit growing areas of California. Tree grown in USDA Hardiness Zone 9. Winter chilling requirement approximately 150 hours at or below 45° F.

Trunk:

*Size.*—Large. Circumference of 44.5 cm at 30.5 cm above ground on a 5 year old tree.

*Stocky.*—Medium stocky.

*Texture.*—Medium shaggy, roughness increases with age.

*Color.*—Varies from 7.5YR 4/2 to 7.5YR 2/4.

Branches:

*Size.*—Medium. Average circumference 14.2 cm at 1.2 meters above ground. Crotch angle approximately 35°, increases with heavy crop load.

*Surface texture.*—New growth relatively smooth. Mature growth medium rough, roughness increases with age.

*Lenticels.*—Average number 27 in a 25.8 square cm area. Average length 3.6 mm. Average width 1.6 mm. Color varies from 7.5YR 6/6 to 7.5YR 6/8.

*Color.*—New growth varies from 2.5GY 6/6 to 5GY 6/6. Old growth varies from 7.5YR 2/4 to 10YR 3/4, varies with age of growth.

Leaves:

*Size.*—Large. Average length 149.2 mm. Average width 47.9 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slightly indented over midrib and leaf veins. Lower surface relatively smooth except for ridges caused by midrib and pinnate venation. Both surfaces glabrous.

*Petiole.*—Average length 10.1 mm. Average width 1.9 mm. Longitudinally grooved. Surface — glabrous. Color varies from 5GY 5/6 to 5GY 4/6.

*Glands.*—Reniform. Size — large. Average length 1.6 mm. Average width 1.1 mm. Number varies from 2 to 4, average number 3. Located primarily on base of leaf blade, upper portion of petiole. Color varies from 7.5Y 7/8 to 10Y 7/6.

*Stipules.*—Average number 2. Average length 8.1 mm. Edges — pectinate. Color varies from 2.5GY 6/8 to 5GY 6/8.

*Color.*—Upper surface varies from 5GY 3/6 to 7.5GY 3/4. Lower surface varies from 5GY 4/4 to 5GY 4/6. Midvein color varies from 2.5GY 7/4 to 2.5GY 6/6.

Flower buds:

*Size.*—Medium. Average length 17.7 mm. Average diameter 10.0 mm.

*Hardiness.*—Hardy with respect to California winters.

*Form.*—Plump, conical, becoming elongated before opening.

*Pedicel.*—Average length 4.8 mm. Average width 1.3 mm. Color varies from 2.5GY 7/10 to 5GY 7/8.

*Color.*—Varies from 2.5RP 8/6 to 5RP 7/8.

Flowers:

*Blooming period.*—Date of First Bloom — Jan. 28, 2012. Date of Petal Fall — Feb. 6, 2012, varies slightly with climatic conditions.

*Size.*—Large. Average height 19.6 mm. Average diameter 41.9 mm.

*Petals.*—Size — large. Number — normally 5, alternately arranged to sepals. Average length 20.5 mm. Average width 19.1 mm. Form — orbicular, narrows at point of attachment. Margin — sinuate. Color varies from 10RP 8/4 to 7.5RP 7/8. Both upper and lower surfaces glabrous.

*Sepals.*—Size — medium to large. Number — normally 5, alternately arranged to petals. Average length 6.2 mm. Average width 5.6 mm. Shape — triangular. Margin — entire. Color — upper surface varies from 10Y 6/2 to 5R 3/6. Lower surface varies from 5GY 5/4 to 2.5GY 6/4. Upper surface glabrous, lower surface pubescent.

*Stamens.*—Average number per flower 49. Average filament length 14.2 mm. Filament color varies from N 9.5/(white) to 5RP 6/6. Anther color varies from 7.5R 3/8 to 2.5Y 8/10.

*Pollen.*—Self-fertile. Color varies from 5Y 7/8 to 2.5Y 7/8.

*Pistil.*—Normally one. Surface glabrous. Average length 21.2 mm. Stigma height average of 1.0 mm above anthers. Color varies from 10Y 8/8 to 7.5Y 7/8.

*Fragrance.*—Moderate.

*Color.*—Varies from 2.5RP 8/4 to 5RP 8/6.

*Number flowers per flower bud.*—One.

*Pedicel.*—Average length 5.3 mm. Average width 1.2 mm. Color varies from 2.5GY 5/8 to 5GY 5/8.

Fruit:

*Maturity when described.*—Firm ripe.

*Date of first picking.*—Apr. 29, 2012.

*Date of last picking.*—May 5, 2012, varies slightly with climatic conditions.

*Size.*—Medium to large. Average diameter axially 59.5 mm. Average transversely in suture plane 60.1 mm. Average weight 120.2 grams, varies slightly with fertility, amount of thinning and climatic conditions.

*Form.*—Globose.

*Suture.*—Shallow, extends from base to apex.

*Ventral surface.*—Very slightly lipped.

*Apex.*—Slightly retuse.

*Base.*—Retuse.

*Stem cavity.*—Rounded to slightly elongated in suture plane. Average depth 2.9 mm. Average diameter 6.6 mm.

Stem:

*Size.*—Small. Average length 9.6 mm. Average diameter 6.6 mm.

*Color.*—Varies from 2.5GY 6/8 to 2.5GY 5/8.

Flesh:

*Ripens.*—Evenly.

*Texture.*—Firm, meaty.

*Fibers.*—Few, small, tender.

*Firmness.*—Good, holds firm on the tree 7 days after maturity (shipping ripe).

*Aroma.*—Moderate.

*Amydgalin.*—Undetected.

*Eating quality.*—Good.

*Flavor.*—Good.

*Juice.*—Moderate amount, enhances flavor.

*Brix.*—Average Brix 11.5°, varies slightly with amount of fruit per tree and climatic conditions.

*Pit cavity.*—Average length 35.0 mm. Average width 24.6 mm. Average depth 11.0 mm. Color 5Y 8/10.

*Color.*—Varies from 2.5Y 8.5/8 to 10YR 7/10.

Skin:

*Thickness.*—Medium.

*Surface.*—Smooth.

*Bloom.*—Wanting.

*Tendency to crack.*—None.

*Color.*—Ground color varies from 5Y 8/8 to 5Y 7/8. Overspread with 7.5R 3/10 to 7.5R 2/8.

*Tenacity.*—Tenacious to flesh.

*Astringency.*—Undetected.

Stone:

*Type.*—Clingstone.

*Size.*—Medium to large. Average length 33.8 mm. Average width 22.8 mm. Average thickness 18.5 mm.

*Form.*—Obovoid.

*Base.*—Varies from round to flat.

*Apex.*—Pointed, average length 1.9.

*Surface.*—Pitted throughout, pits vary from round to elongated.

*Sides.*—Unequal, one side extending further from suture plane.

*Ridges.*—Relatively smooth, extending from base to apex.

*Tendency to split.*—Slight.

*Color.*—Varies from 2.5Y 9/2 to 10YR 5/8 when dry.

Kernel:

*Size.*—Medium. Average length 18.4 mm. Average width 11.5 mm. Average depth 6.5 mm.

*Form.*—Ovate.

*Viability.*—Poor, embryo only partially developed.

*Skin color.*—Varies from 5Y 9/2 to 7.5Y 9/2.

Use: Dessert.

*Market.*—Local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

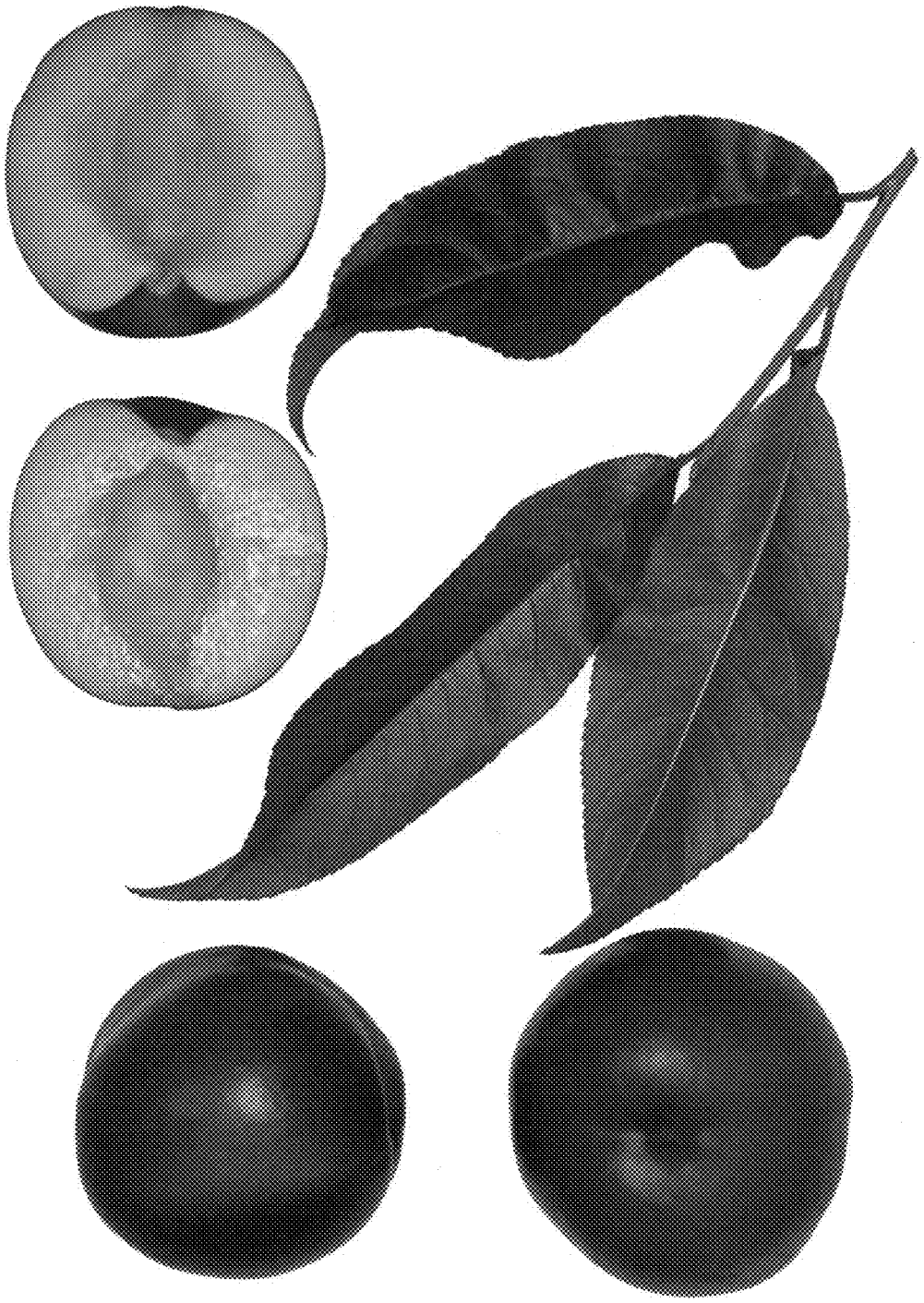

* * * * *